United States Patent [19]

Breuil et al.

[11] Patent Number: 4,988,539
[45] Date of Patent: Jan. 29, 1991

[54] METHOD OF MANUFACTURING A GAS DETECTION SENSOR, AND THE RESULTING SENSOR

[75] Inventors: Philippe Breuil, Saint-Etienne; Christophe Pijolat, La Talaudiere; Guy Tournier; Lalauze René, both of Saint-Etienne, all of France

[73] Assignee: Association pour la Recherche et le Developpment des Methodes et Processus Industriels - Armines, Paris, France

[21] Appl. No.: 446,545

[22] Filed: Dec. 6, 1989

[30] Foreign Application Priority Data

Dec. 6, 1988 [FR] France ................................ 88 15975

[51] Int. Cl.$^5$ ................................................ B05D 5/12
[52] U.S. Cl. ................................ 427/126.3; 427/255.2; 427/255.3
[58] Field of Search ................ 427/126.3, 255.2, 255.3

[56] References Cited

U.S. PATENT DOCUMENTS 4,504,522  3/1985  Kaiser et al. .

FOREIGN PATENT DOCUMENTS 2029583  3/1980  United Kingdom .

OTHER PUBLICATIONS

Extended Abrstracts, vol. 80-2, Oct. 1980, pp. 1367-1369, résumé No. 547, Princeton, N.J., U.S.; H. Ogawa et al.: "A new type ultrafine particle gas sensor".

*Primary Examiner*—Stanley Silverman
*Attorney, Agent, or Firm*—Griffin, Branigan & Butler

[57] ABSTRACT

A method of manufacturing a sensor for detecting trace or impurity gases, the method comprising evaporating tin and/or tin oxides under a partial pressure of oxygen in order to condense vapor on an electrically insulating substrate to obtain a porous layer deposit therein. The metal or the metal oxides is/are evaporated under a flow of a mixture of gases containing both oxygen and an inert gas at a total pressure of not less than 100 pascals and with the partial pressure of the oxygen in the mixture being not more than 130 pascals.

5 Claims, No Drawings

METHOD OF MANUFACTURING A GAS DETECTION SENSOR, AND THE RESULTING SENSOR

The present invention relates to a method of manufacturing a sensor for detecting trace or impurity gases in an atmosphere under surveillance by measuring the electrical conductivity of a porous layer of tin oxides.

BACKGROUND OF THE INVENTION

Use is made of the variation in the conductivity of such metal oxides both as a function of temperature and as a function of the presence of certain gases for the purpose of detecting trace or impurity gases in an atmosphere being monitored.

One of the factors influencing this variation and relating to the presence of a gas is chemisorption i.e. the transfer of electrons between the gas and the oxide. Thus the absorbed gas either takes electrons from the semiconductive oxide, or else it gives them up to it. Depending on the P or N type of the semiconductor and the donor or acceptor character of the gas, the conductance increases (P & acceptor or N & donor) or decreases (N & acceptor or P & donor). It will be understood that sensor sensitivity depends on there being as many occasions as possible for exchange to take place between the gas and the semiconductor. For a given quantity of deposited oxide, it is necessary to have as large an exchange area as possible, and thus to look for ways of making the layer as uncompact as possible.

Known methods of manufacturing such sensors are based on vacuum depositing a semiconductive metal oxide (e.g. tin dioxide: $SnO_2$). In outline the procedure is as follows. A vacuum is established down to about $10^{-4}$ Pa in a chamber containing an insulating substrate and a crucible raised to a temperature lying in the range 1100° C. to 1300° C., and a flow of oxygen at about 10 Pa to 20 Pa is injected. $SnO_2$ is deposited on the substrate situated in the chamber at a few centimeters from the crucible, with deposit being in a layer having the well-known column structure which, while not compact, does not offer sufficient sites for chemisorption activity for a sensor of this type to be very great sensitivity.

If the oxygen pressure is increased at the moment of evaporation to as much as 130 Pa or more, the structure of the deposited layer changes and becomes spongy, which is more favorable for obtaining acceptable sensitivity. However, such high oxygen pressure causes the refractory metal of the crucible to oxidize, with the resulting oxides being entrained towards the substrate where they pollute the deposited spongy layer, thereby destroying the sensitivity of the sensor.

The invention is the result of work during which a certain number of phenomena that control the formation of a homogeneous spongy layer have been established.

SUMMARY OF THE INVENTION

It is in this way that one of the main characteristics of the method of the invention was determined, i.e. that the metal oxide should be evaporated in a flow of gas necessarily containing oxygen and an inert gas so as to obtain a total pressure compatible with building a spongy structure (between about 100 Pa to about 200 Pa) while avoiding polluting the layer with refractory metal oxides because the presence of oxygen in the mixture is limited to a partial pressure lying in the range 20 Pa to 130 Pa, and preferably in the range 20 Pa to 80 Pa.

A very acceptable mixture is a mixture of oxygen and nitrogen in the same ratio as in natural air, with the total pressure being adjusted to between 100 Pa and 200 Pa. The pressure depends on a large number of factors, with the most important being the distance between the substrate and the crucible.

The work has shown that the oxygen in contact with the bath of molten tin oxidizes the surfaces of the bath, with the oxide then being sublimed. It is highly likely that a spongy structure results from this oxide vapor condensing prior to reaching the substrate, with the condensation being due to the vapor molecules cooling during the shocks to which they are subjected in the flow of gas, the shocks being between one another and with the molecules of the flow. Thus a spongy structure is generated by a certain "density" of flow, and the shorter the distance between the crucible and the substrate, the greater the "density" needed in order to ensure an equivalent number of occasions on which shocks can occur. The flow must also be rich enough in oxide and thus in initial oxygen to prevent the time required for deposition becoming too long.

By way of example, if the crucible-to-substrate distance is about 3.5 cm, then the total pressure should be about 100 Pa to 120 Pa, whereas if the distance is about 2 cm, then the pressure should be about 150 Pa to 160 Pa.

In addition, the work has also shown that there is a minimum quantity of oxygen that is required for tin oxidation to take place. This quantity depends on the temperature of the bath, and in terms of oxygen partial pressure it is a few Pa.

Finally, it is observed that there is also a limit on the total pressure of the gas flow, which limit depends largely on the geometry of the vacuum deposition chamber. At above 250 Pa to 300 Pa convection phenomena occur which give rise to non-uniformities in the deposit and make stable and reproducible manufacture impossible. In any event, sensors manufactured experimentally at higher pressures do not exhibit any significant improvement in their response characteristics.

The electrodes for making contact with the thin layer deposited on the resistive substrate are constituted by fine layer of gold deposited on the substrate either before or after the deposition of tin oxides.

Naturally, the method of the invention allows for the quantity of oxides deposited to be controlled by adjusting the distance between the crucible and the substrate and/or by adjusting the duration of the exposure to metal vapor. As a result, the temperature at which the sensor is most sensitive in use can be adjusted in this way. The variation in the conductance of such a sensor in the presence of a given gas varies as a function of the measurement temperature. There is often a very marked sensitivity maximum at a well-defined temperature depending, inter alia, on the thickness of the porous layer, which layer is easily adjusted using the method of the invention.

We claim:

1. A method of manufacturing a sensor for detecting trace or impurity gases, the method comprising evaporating tin and/or tin oxides under a partial pressure of oxygen in order to condense vapor thereof on an electrically insulating substrate to obtain a porous layer deposit thereon, wherein the evaporation of the metal or the metal oxides is performed under a flow of a mixture of gases containing both oxygen and an inert gas at a total pressure lying in the range 100 Pa to 200 Pa and with the partial pressure of the oxygen in the mixture lying in the range 20 Pa to 130 Pa.

2. A method according to claim 1, wherein the partial pressure of the oxygen in the mixture is not more than 80 Pa.

3. A method according to claim 1, wherein the partial pressure of the oxygen is about one-fifth of the total pressure.

4. A method according to claim 1, wherein connection electrodes are made by depositing a layer of previously-evaporated gold on the support, either before or after building up the porous metal oxide layer.

5. A sensor for detecting trace or impurity gas made by the method of claim 1, wherein the matal oxide layer has spongy structure which is free from oxides of the material from which the evaporation crucible is made.

* * * * *